United States Patent [19]

Wright et al.

[11] 4,200,756
[45] Apr. 29, 1980

[54] METHYL 3-(3-ETHYLUREIDO)-1,2,5,6-TETRAHYDRO-2-OXOPYRIDINE-4-CARBOXYLATE

[75] Inventors: George C. Wright; Ronald E. White, both of Norwich, N.Y.

[73] Assignee: Morton-Norwich Products, Inc., Norwich, N.Y.

[21] Appl. No.: 967,366

[22] Filed: Dec. 7, 1978

[51] Int. Cl.$^2$ .................................... C07D 211/90
[52] U.S. Cl. ............................ 546/297; 424/266; 546/298
[58] Field of Search ............................... 546/297, 298

[56] References Cited

U.S. PATENT DOCUMENTS

| | | | |
|---|---|---|---|
| 2,947,754 | 8/1960 | Scudi et al. | 546/298 |
| 3,632,851 | 1/1972 | Schmitt et al. | 546/298 |
| 3,660,486 | 5/1972 | Thiele | 546/298 |
| 4,108,630 | 8/1978 | Johnson et al. | 546/298 |

*Primary Examiner*—Alan L. Rotman
*Assistant Examiner*—Natalia Harkaway
*Attorney, Agent, or Firm*—Anthony J. Franze

[57] ABSTRACT

Methyl 3-(3-ethylureido)-1,2,5,6-tetrahydro-2-oxopyridine-4-carboxylate is useful as a muscle relaxant.

1 Claim, No Drawings

METHYL 3-(3-ETHYLUREIDO)-1,2,5,6-TETRAHYDRO-2-OXOPYRIDINE-4-CARBOXYLATE

This invention relates to the chemical compound methyl 3-(3-ethylureido)-1,2,5,6-tetrahydro-2-oxopyridine-4-carboxylate. It possesses pharmacologic activity. Particularly, it exhibits skeletal muscle relaxant activity when administered to warm blooded animals. Upon intravenous administration of it to rats in a dose of about 25 mg/kg, inhibition of gastrocnemius muscle twitch is elicited. Suitable vehicles for intravenous administration include physiologically acceptable menstrua such as dimethylsulfoxide, tetrahydrofuryl alcohol and dimethylacetamide.

The compound of this invention can be readily formulated into pharmaceutical compositions such as tablets, elixirs, solutions, suspensions, capsules and the like using excipients and adjuvants commonly employed for such purposes and with which there is no incompatibility.

In order that this invention may be readily available to and understood by those skilled in the art, the following method of preparing it is described:

A. Ethyl 2,3-Dioxo-4-piperidinecarboxylate

A few crystals of iodine and a small amount of $Hg_2Cl_2$ were introduced into a mixture of benzene (2 liters) and ethanol (280 ml). Sodium methoxide (108 g, 2.0 moles) was added with stirring. A mixture of 2-pyrrolidone (17.2 g, 2.0 moles) and diethyl oxalate (292 g, 2.0 moles) was introduced in large increments. Slight exothermicity was observed. The reaction mixture was refluxed for 24 hours. It was acidified with 320 ml of 1:1 HCl. The hot benzene was decanted, the salt and water were mixed with fresh boiling benzene, and the benzene was decanted. This extraction with boiling benzene was done three times. The extracts were combined and filtered by gravity. The filtrate was concentrated under reduced pressure to approximately 1.5 liters. This was concentrated on a steam bath to approximately 600 ml. On cooling overnight, a solid (151 g, m.p. 148°–151°) was obtained. Yield: 40.7%.

B. Methyl 2,3-Dioxoisonipecotate

To a solution of sodium methylate (40 g, 0.74 mole) in methanol (14 liters) was added A (2000 g, 10.8 moles). The mixture was refluxed 120 hours then filtered through a 2 inch thick bed of filter aid. The resulting filtrate was reduced in volume on a Calab evaporator to approximately 2500 ml and refrigerated overnight. The product was isolated by filtration and washed by stirring in ether (3 liters). After drying at 60°, there was obtained 1070 g (58%), m.p. 151°–3° (Mel-Temp. Uncorr.). Recrystallization of a small sample from methanol gave an analytical sample which melted at 155°–6°.

Anal. Calcd. for $C_{11}H_{18}N_2O_5$: C, 49.12; H, 5.30; N, 8.18. Found: C, 49.02; H, 5.53; N, 8.07.

C. Methyl 3-Benzyl-1,2,5,6-tetrahydro-2-oxopyridine-4-carboxylate

A mixture of B (188 g, 1.10 mole), toluene (3030 ml), and benzylamine (123 ml, 1.1 mole) was treated with conc. HCl (1.1 ml) and refluxed (with a Dean-Stark trap) for 7 hours, until all of the $H_2O$ (20.1 ml) was removed. The reaction mixture was filtered to remove a small amount of insoluble material, and the filtrate was concentrated to dryness under reduced pressure. Recrystallization of the residue from methanol (550 ml) gave crystalline product which was washed with cold methanol (100 ml) and ether; m.p. 104°–108°; Yield: 212 g (74.2%).

Anal. Calcd. for $C_{14}H_{16}N_2O_3$: C, 64.60; H, 6.20; N, 10.78 Found: C, 64.72; H, 6.33; N, 10.78.

D. Methyl 3-Amino-1,2,5,6-tetrahydro-2-oxopyridine-4-carboxylate

A mixture of C (65 g, 0.25 mole), methanol (740 ml), and 5% Pd/C, 50% $H_2O$ (32 g) was subjected to hydrogenation in a stainless steel canister. A pressure drop of 17.1 psia. (theory: 16.7 psia.) was observed, over 2 hours. The reaction solution was filtered of catalyst and concentrated under the water pump to dryness. The residue was washed with ether, and then warmed with acetone (400 ml) and cooled in the refrigerator. Crystalline product was collected by filtration; m.p. 192°–194°, Yield: 12 g.

Anal. Calcd. for $C_9H_{10}N_2O_3$: C, 49.40; H, 5.92; N, 16.46. Found: C, 49.74; H, 6.05; N, 16.32.

E. Methyl 3-(3-ethylureido)-1,2,5,6-tetrahydro-2-oxopyridine-4-carboxylate

The compound of D (46.0 g, 0.27 mole) and benzene (1350 ml) was refluxed for 1.5 hour using a Dean-Stark trap to remove residual water. The cooled solution was treated with ethyl isocyanate (92.0 ml, 1.3 moles) and triethylamine (18.0 ml). The resultant solution was refluxed for 16 hours, and then stripped of solvent under the water pump. Benzene (300 ml) was added to the residue, then removed under the water pump. The residue was dissolved in ether, filtered, and stripped of ether. Recrystallization from methanol (100 ml) gave a crystalline product. A second recrystallization from methanol (300 ml) gave cream-colored crystals; m.p. 103°, yield: 40 g (51%).

Anal. Calcd. for $C_{10}H_{15}N_3O_4$: C, 49.78; H, 6.28; N, 17.42. Found: C, 50.19; H, 6.39; N, 17.14.

What is claimed is:
1. The compound methyl 3-(3-ethylureido)-1,2,5,6-tetrahydro-2-oxopyridine-4-carboxylate.

* * * * *